United States Patent
Balasundram et al.

(10) Patent No.: US 8,790,722 B2
(45) Date of Patent: Jul. 29, 2014

(54) BOTANICAL EXTRACT FROM THE AQUEOUS STREAM OF THE PALM OIL MILLING PROCESS FOR THE PREVENTION AND INHIBITION OF OXIDATIVE STRESS AND HAEMOLYSIS IN HUMAN RED BLOOD CELLS

(75) Inventors: Nagendran Balasundram, Selangor (MY); Ravigadevi Sambanthamurthi, Selangor Darul Ehsan (MY); Yew Ai Tan, Kuala Lumpur (MY); Kalyana Sundram P. Manickam, Selangor Darul Ehsan (MY); Mohd Basri bin Wahid, Selangor Darul Ehsan (MY); Samir Samman, Sydney (AU); Nihal S. Agar, Sydney (AU)

(73) Assignee: Malaysian Palm Oil Board, Kajang, Selangor (MY)

( * ) Notice: Subject to any disclaimer, the term of this patent is extended or adjusted under 35 U.S.C. 154(b) by 431 days.

(21) Appl. No.: 12/677,764

(22) PCT Filed: Sep. 11, 2008

(86) PCT No.: PCT/MY2008/000100
§ 371 (c)(1),
(2), (4) Date: Nov. 16, 2010

(87) PCT Pub. No.: WO2009/035314
PCT Pub. Date: Mar. 19, 2009

(65) Prior Publication Data
US 2011/0052728 A1  Mar. 3, 2011

(30) Foreign Application Priority Data
Sep. 11, 2007  (MY) ................. PI20071517

(51) Int. Cl.
*A61K 36/899* (2006.01)
*A61K 8/97* (2006.01)
*A61K 35/14* (2006.01)

(52) U.S. Cl.
USPC .......................................... 424/727; 424/529

(58) Field of Classification Search
None
See application file for complete search history.

(56) References Cited

U.S. PATENT DOCUMENTS

2003/0031740 A1* 2/2003 Sambanthamurthi et al. ........................... 424/777

OTHER PUBLICATIONS

Davies. Oxidative Sress: The paradox of aerobic life. Biochem Soc Symp. 1995. 61. Abstract.*
Ganafa et al (Effect of palm oil on oxidative stress-induced hypertension, American Journal of Hypertension 15, 725-731 (Aug. 2002)).*
Davies, KJ, ( Oxidative Stress, the paradox of aerobic life, Biochem Soc. Symp., 1995, 61:1-31).*
Balasundram et al. ( Antioxidant properties of palm fruit extracts, Asia Pac. J Clinical Nutrition, 2005: 4(4):319-324).*
Agar, et al, Role of catalase in H2O2-induced oxidant stress in Marsupial Erythrocytes, Compo Haematol. Int., 6:32-34 (1996).
Balasundram, et al., Antioxidant properties of palm fruit extracts. Asia Pacific Journal of Clinical Nutrition, 14(4):319-324 (2005).
International Search Report dated Jun. 12, 2009 in related PCT Appl Serial No. PCT/MY2008/000100.
Sundram, et al., Palm fruit chemistry and nutrition, Asia Pacific Journal of Clinical Nutrition, 12(3): 355-362 (2003).

* cited by examiner

Primary Examiner — Chris R Tate
Assistant Examiner — Deborah Davis
(74) Attorney, Agent, or Firm — Foley & Lardner LLP

(57) ABSTRACT

The invention provides a composition for the prevention and inhibition of oxidative stress and hemolysis in human red blood cell wherein said composition compounds obtained from the aqueous stream of palm oil milling (palm oil vegetation liquor), in particular from vegetative liquor from the milling of palm oil fruit.

2 Claims, 4 Drawing Sheets

BOTANICAL EXTRACT FROM THE AQUEOUS STREAM OF THE PALM OIL MILLING PROCESS FOR THE PREVENTION AND INHIBITION OF OXIDATIVE STRESS AND HAEMOLYSIS IN HUMAN RED BLOOD CELLS

CROSS-REFERENCE TO RELATED APPLICATIONS

This application is a Divisional Patent Application of U.S. Utility patent Ser. No. 12/677,764, filed Nov. 16, 2010, which is the U.S. national stage application under 35 U.S.C. §371 of International Patent Application No. PCT/MY2008/000100, filed on Sep. 11, 2008, which claims priority to Malaysian Patent Application No. PI20071517, filed on Sep. 11, 2007, each of which is incorporated herein by reference in its entirety.

FIELD OF INVENTION

The present invention relates to the use of a composition for the prevention and inhibition of haemolysis; in particular the invention relates to a composition obtained from the aqueous stream of palm oil milling (palm oil vegetation liquor) for the prevention and inhibition of oxidative stress and haemolysis in human red blood cells (RBC).

BACKGROUND OF INVENTION

Haemolysis can be considered as the final intracellular event in regards to impairment of a human erythrocyte affected by oxidative distress. In this condition, the human erythrocyte or red blood cells (RBC), is break open and consequently hemoglobin is released into the plasma.

The intracellular events of human erythrocytes or red blood cells upon induced by any oxidative agents may include cell morphological transformations or alteration, enzyme modifications, depletion of intracellular glutathione (GSH) and haemolysis. Comprehendingly, the prevention of oxidative stress facilitates to inhibit potential red blood cells impairment.

Invariable medical research and investigations conducted over several years on the deformability or impairment of human red blood cells (RBC) has perceived that, apart from the deficiency on glucose-6-phosphate dehydrogenase (G6PD), extraordinary amount of reactive oxygen species, including free radicals production and increased level of radical-generating substance are primary causative factors in relation to haemolysis of the human red blood cells (RBC).

The indirect surplus of free radicals and oxidants is induced by environmental causes or disrupted physiological processes, one of the most common physiological processes complications include the failure of human biological system's ability to detoxify reactive intermediates or damages. Such condition will gradually result to oxidative distress of the blood cells.

Critical level of oxidative distress in human blood cell may result to tissue injury related diseases, including cardiovascular disease or neurodegenerative disease, while haemolysis leads to haemolytic anemia, whereby in this condition, the bone marrow activity cannot counteract the high amount of red blood cells disruption.

Haemolysis can be reduced by prevention or protection of the blood cells from oxidative distress. One of the most effective amelioration methods in this regard is the presence of free radical defense.

Free radical defense may include the supplementation of antioxidants which play a major role in alleviating the destructive effects of excessive oxidants and free radicals, either in cellular or supplemented forms. Examples of cellular antioxidants are enzymes superoxide dismutase (SOD), catalase and gluththione peroxidase, wherein these enzymes function as free radical scavengers and chain reaction terminators. Chemical antioxidants however act by donating electron to a free radical and thus converting it into a non-radical form.

Another widely known medical application involving antioxidants or free radicals scavengers is from a plant based source. It is evident nowadays that the primary constituents based on plant extracts having astronomical medicinal properties comprise antioxidants which are in the form of phenolics and flavanoids. These antioxidants are preferred compared to chemical antioxidants as they have lower risks of releasing or forming their own free radical upon scavenging a free radical. It follows that the use of compositions containing extracts based on plant having antioxidant properties instead of synthetic or chemical antioxidants for treatment of various diseases are now gaining momentum. An exemplary of an excellent source of two major phytochemicals namely vitamin E (tocopherols and tocotrienols) and carotenoids, both of which are fat soluble, is the oil palm fruit. Palm vitamin E has been reported to act as a potent biological antioxidant, protecting against oxidative stress and the atherosclerotic process.

Palm fruit (*Elaeis guineensis*) extracts have been reported to exhibit scavenging activity in relation to reactive oxygen species, via hydrogen- and electron-donating mechanisms.

It is the primary objective of the present invention to provide a composition for preparing a medicament for the prevention of oxidative stress and haemolysis to human red blood cells (RBC), based on a plant extract.

It is further an objective of the present invention to provide a composition for preparing a safe medicament for the prevention of impairment of human red blood cell due to oxidative stress and haemolysis, said composition containing palm oil phenolics.

SUMMARY OF INVENTION

The present invention relates to a composition comprising phenolics and flavanoids obtained from the aqueous stream of palm oil milling, for the prevention and inhibition of oxidative stress and haemolysis in human red blood cell.

The invention further relates to a use of therapeutically effective amount of a composition containing the said palm oil extracts in the preparation of a medicament for prevention and inhibition oxidative stress and haemolysis in human red blood cell in an individual by administering to an individual in need thereof.

DETAILED DESCRIPTION OF THE INVENTION

Figure 1:
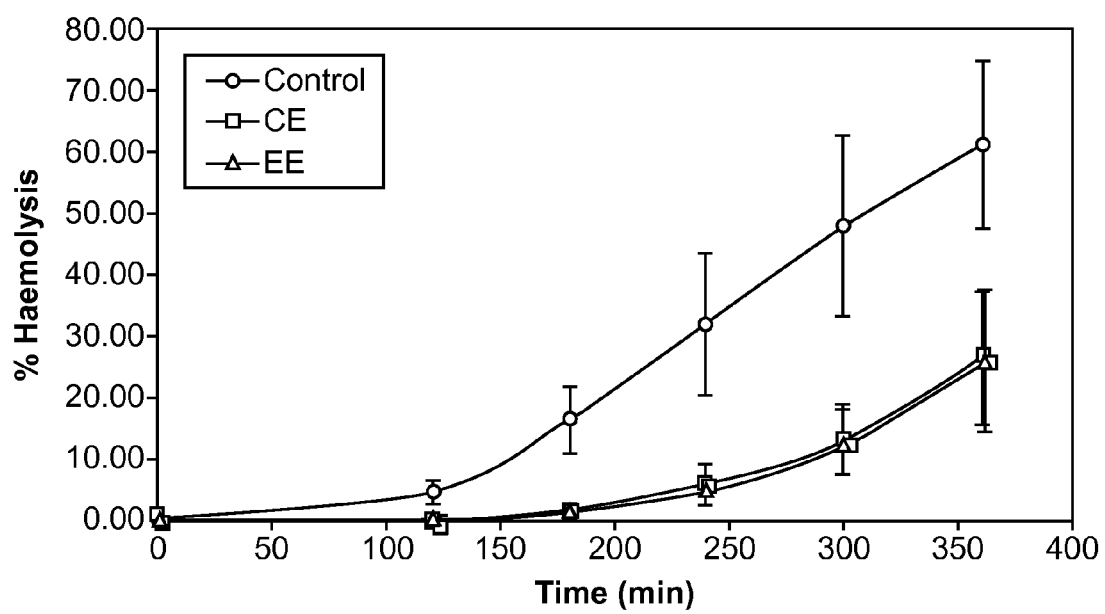
FIG. 1: Results on the effects of extracts of the present invention on haemolysis.

The present invention relates to the identification of excellent remedial effects for the prevention of oxidative stress and haemolysis in human red blood cells (RBC) based on palm phenolics and vitamin E, and thus the production of a composition on the same.

Erythrocytes are suitable models for studies on oxidative stress and human erythrocytes have been used as model systems to investigate the antioxidant activity of natural extracts from black tea, and turmeric, as well as polyphenol-rich fractions from tea, virgin olive oil and red wine.

The following experiments was conducted to show that Palm fruit (Elaeis gunieensis) exhibits antioxidant activity, acting as scavengers of reactive oxygen species via hydrogen- and electron-donating mechanisms and to evaluate the antioxidant properties of palm fruit crude extract referred herein as CE and ethanolic extract referred as (EE).

For the purpose of this invention, the said experiments was conducted in an ex vivo model system using human red blood cells (RBC). Blood sample was obtained from healthy volunteers and collected in heparinized tubes.

The methods and results obtained based on respective assays to determine the effectiveness of the said compounds in palm oil vegetation liquid will be described herein. The preferred embodiments of the present invention will now be illustrated by way of a working example.

BEST MODE FOR CARRYING OUT THE INVENTION

Working Example

Materials 2,2'-azobis-(2-amidinopropoane)dihydrochloride (AAPH) was obtained from Wako Pure Chemical Co., Ltd. All other reagents used were of analytical grade.

The biologically active extracts of palm vegetation liquor useful in this invention can be prepared by any means capable of extracting phenolic compounds from the vegetation liquor using standard extraction techniques or techniques as described in U.S. Patent Application No. 20030031740 (Sambanthamurthi, Tan and Sundram 2004). Such extractions include but are not limited to ethanol, methanol, acetone, ethyl acetate and butanol.

The extract as described in the above patent (referred herein as crude extract CE) and ethanolic extracts (EE) were prepared, wherein the extracts were successfully recovered from the vegetation liquor generated from the milling of oil palm fruits.

Fresh blood was obtained from healthy volunteers by venipuncture, and collected in heparinized test tubes.

METHODS AND RESULTS

Methods

I. Haemolysis of Erythrocytes

Blood was centrifuged at 3000 RPM for 20 minutes. Subsequently, the plasma and buffy coat were removed by aspiration. The RBCs were washed three times with 10 mM phosphate buffered saline (PBS) pH 7.4 and resuspended in the same buffer to yield a haematocrit (Hct) of 10% when incubated at 37° C. with 50 nM 2,2'-azobis-(2-amidinopropoane)dihydrochloride (AAPH), without extracts—referred herein as Control, or with CE or EE at a final concentration.

Accordingly, palm fruit extracts in PBS were added to final concentration of 0.025 to 0.10 mM GAE before addition of 50 mM in AAPH in PBS. For control samples, an equivalent volume of PBS was added before the addition of AAPH. Samples were then incubated in a shaking water bath 37° C., and aliquots were taken at timed intervals for determination of degree of haemolysis, GSH concentration and MetHB content. The degree of haemolysis was determined according to the conventional method of Zou et al. The concentration of GSH was determined by reaction with 5,5'-dithiobis (2-nitrobenzoic acid (DTNB) according to the method of Buetler. MetHb was measured by spectrophotometric II. Methaemoglobin Formation in Haemolysates Haemolysates were prepared by suspending 40 µL packed RBCs in 10 mL of phosphate buffer (15 mM, pH 7.2). The suspension was vortexed and then centrifuged at 4000 RPM for 10 min. The haemoglobin (Hb) content of the supernatant was adjusted to 100 mg Hb/dL with phosphate buffer (PB). A total amount of 100 µL of extract solution in PB was added to 0.8 mL of haemolysate in a microcuvette. Oxidation was initiated by addition of 100 µL 18 mM $NaNO_2$ and the absorbance at 630 nm was continuously monitored. For the control, 100 µL of buffer was used in place of the extract solution.

Results

FIG. 1 depicts the effects of extracts of the present invention on haemolysis.

AAPH

In the first series of experiments, red blood cell (RBC) suspensions (10% Hct) were incubated with AAPH (50 mM) alone or in the presence of 0.1 mM CE and EE. The graph plotted the progression of AAPH-induced haemolysis of human RBCs, which increases over time. It is shown that the degree of haemolysis is reduced in the presence of CE and EE of the present invention, while there is a long lag time before the onset of haemolysis. This indicates that both extracts effectively protect RBCs against ROS-induced cytotoxicity.

Figure 2:
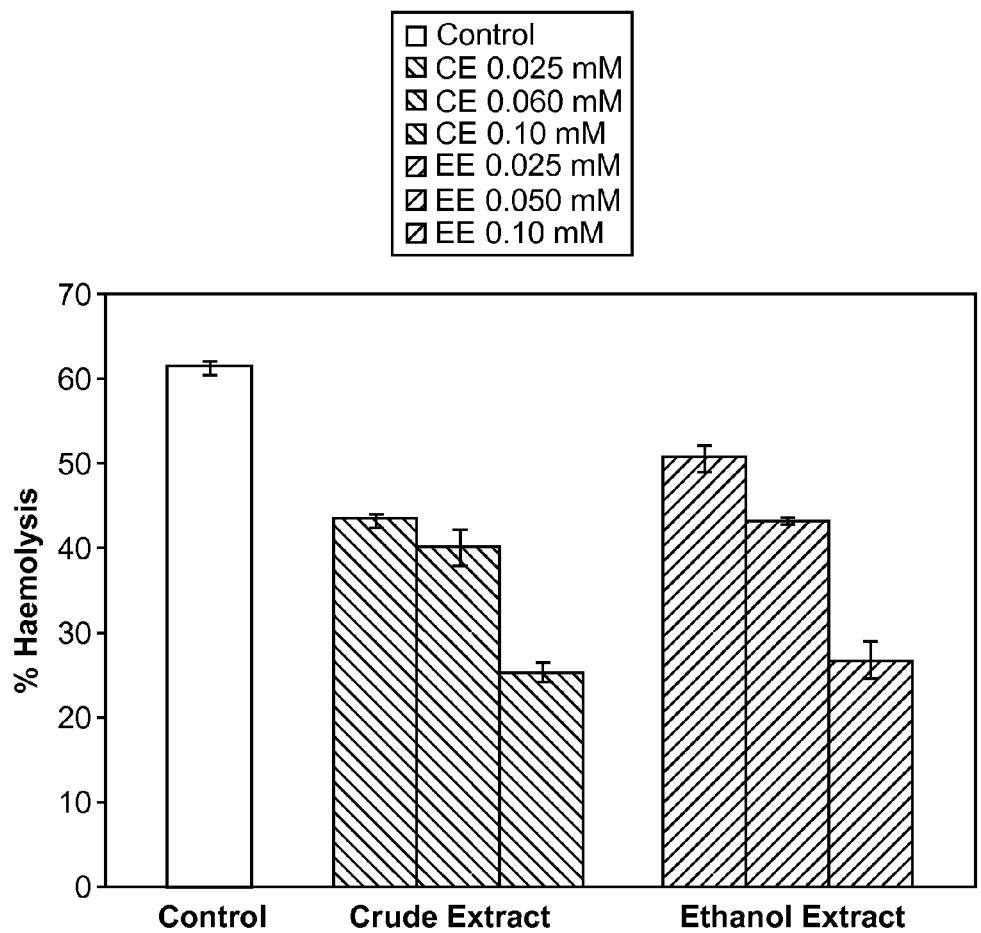
FIG. 2: Results on the protective effect of the present invention on erythrocytes.

FIG. 2 depicts that the protective effect of CE and EE of the present invention on erythrocytes was found to be dose-dependent and a significant protective effect was seen even at a concentration as low as 25 µM GAE of extract. Hydrophillic radical scavenging antioxidants have been found to be effective in preventing AAPH-induced oxidation, as shown in the plotted graph.

In accordance to a preferred embodiment of the present invention, the protective effect of the extracts of the invention may be due to their ability to scavenge peroxyl radicals produced in the aqueous phase before these radicals cause oxidative damage to the RBC membrane.

$NaNO_2$

The second series of experiments for the purpose of the present invention involved the evaluation of the effectiveness of the extracts in inhibiting nitrite-induced oxidation of haemoglobin (Hb) to methaemoglobin (MetHb). Nitrite is a well known oxidizing and MetHb-forming agent.

In this experiment, the haemolysates (100 mg/dL) were incubated with:

A. For Crude Extract (CE)
  a) Added with $NaNO_2$ (1.8 mM) without extracts (Control);
  b) Added with CE 0.05 to 0.10 mM GAE B. For Ethanol Extract (EE)
  a) Added with $NaNO_2$ (1.8 mM) without extracts (Control)
  b) Added with EE 0.05 to 0.10 mM It is shown that the extracts in both forms inhibited the formation of MetHb in haemolysates, and the effect was seen to be dose-dependent as shown in Table 1 below.

TABLE 1

MetHb formation in haemolysates after
10 min incubation with NaNO$_2$ (1.8 mM).

| Treatment | Conc (mM GAE) | MetHb (%) |
| --- | --- | --- |
| Control | 0 | 100 |
| Crude Extract | 0.050 | 87.8 ± 1.3 |
| | 0.075 | 54.7 ± 0.2 |
| | 0.10 | 29.5 ± 2.1 |
| Ethanol Extract | 0.050 | 82.9 ± 0.9 |
| | 0.075 | 53.5 ± 4.5 |
| | 0.10 | 21.1 ± 0.6 |

Values are mean ± SD (n = 4)

For the first series of the experiment and as shown in FIG. 2, the degree of haemolysis in the Control was 64.3±14.6% compared with 25.9±11.7% and 24.38±12.9% for RBC treated with CE and EE respectively. No consistent effects were observed in GSH and MetHb concentrations over 6 hours.

Figure 3:
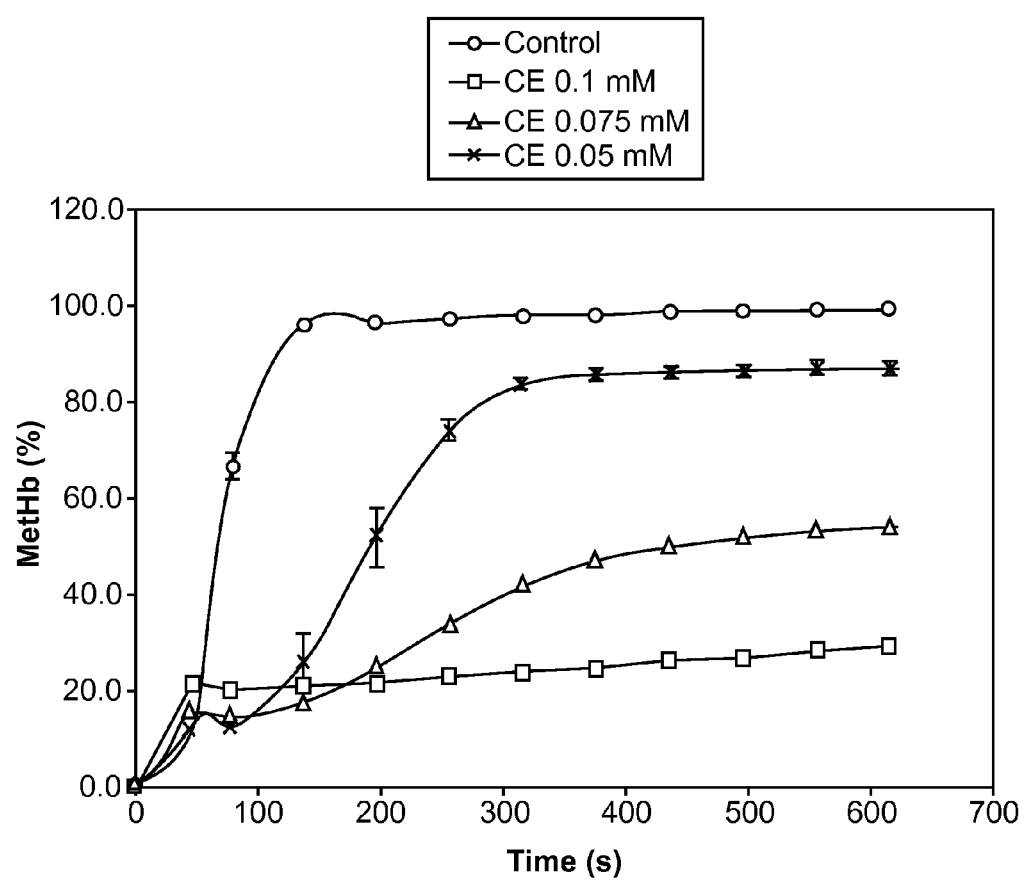
FIG. 3: Effect of Extract (CE) on MetHb formation in haemolysates.
Figure 4:
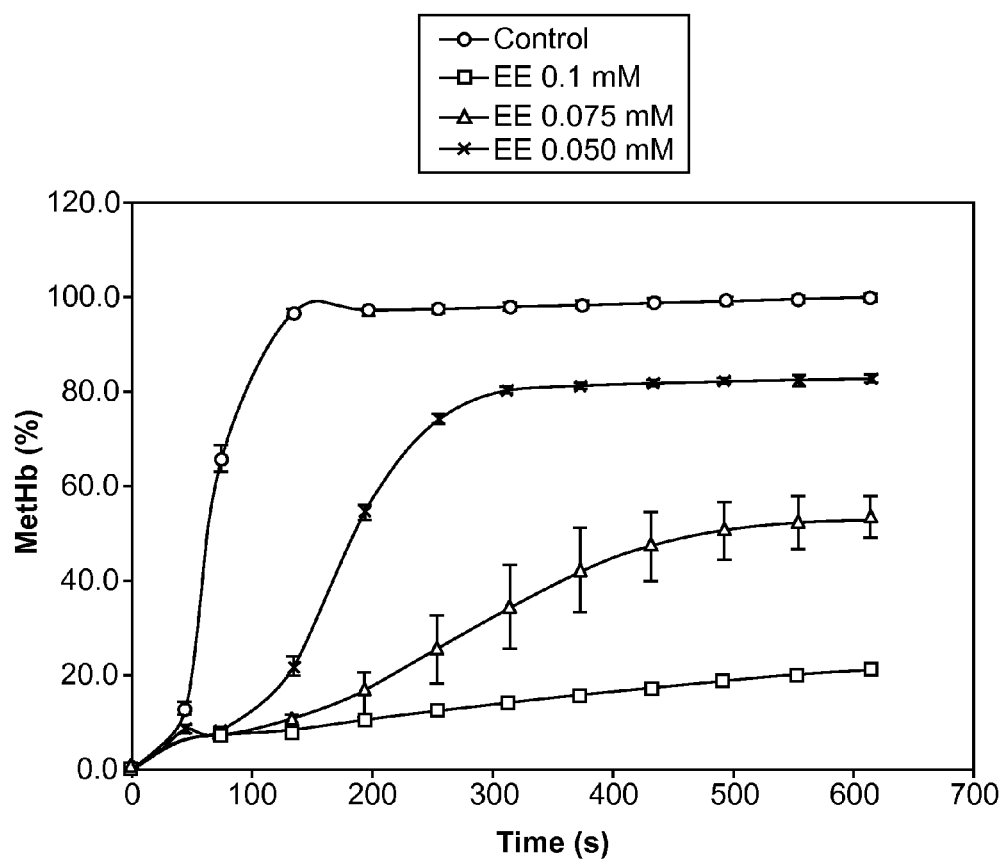
FIG. 4: Effect of EE on MetHb formation in haemolysates.

Based on the plotted graphs (FIG. 3 and FIG. 4), for the second series of the experiment in accordance to the present invention, the changes in the amount of MetHb formed in relation to time at different extract concentrations. The oxidation of Hb to MetHb by nitrite comprise a biphasic reaction, the first phase was an initial lag phase followed by a rapid autocatalytic phase. During the lag phase the MetHb formed may have reacted with H$_2$O$_2$ to generate the ferrylhaemoglobin radical and thus accomplished the autocatalytic phase.

The autocatalytic process is however slowed down in the presence of the extracts of the present invention.

It is therefore concluded that the extracts of the present invention can protect the RBCs from oxidative distress and thus haemolysis by way of inhibiting the rapid progression of MetHb formation, due to the scavenging of H$_2$O$_2$ generated, as evident during the lag phase. In addition, the results also suggest that palm fruit extracts delayed AAPH-induced haemolysis in human red blood cells.

The working example is not intended, however, to limit or restrict the scope of the invention in any way and should not be construed as providing conditions, parameters, reagents or starting materials which must be utilized exclusively in order to practice the present invention.

The invention claimed is:

1. A method for inhibition of oxidative impairment in human red blood cells (RBC) in an individual in need thereof, said method comprising administering to said individual a therapeutically effective amount of a composition comprising phenolic acids and flavonoids obtained from the aqueous stream of palm oil milling (palm oil vegetation liquor).

2. The method of claim 1 wherein said oxidative impairment is due to oxidative stress and haemolysis.

* * * * *